United States Patent
Storbeck et al.

(10) Patent No.: US 9,901,706 B2
(45) Date of Patent: Feb. 27, 2018

(54) CATHETERS AND CATHETER SHAFTS

(71) Applicant: Boston Scientific Scimed, Inc., Maple Grove, MN (US)

(72) Inventors: Gene Thomas Storbeck, South Windsor, CT (US); Timothy Lawrence Rubesch, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 273 days.

(21) Appl. No.: 14/683,709

(22) Filed: Apr. 10, 2015

(65) Prior Publication Data

US 2015/0290423 A1   Oct. 15, 2015

Related U.S. Application Data

(60) Provisional application No. 61/978,551, filed on Apr. 11, 2014.

(51) Int. Cl.
*A61F 11/00* (2006.01)
*A61M 25/00* (2006.01)
*A61L 29/04* (2006.01)
*A61L 29/06* (2006.01)
*A61L 29/14* (2006.01)
*A61L 31/06* (2006.01)
*A61L 31/14* (2006.01)

(52) U.S. Cl.
CPC ....... *A61M 25/0012* (2013.01); *A61L 29/041* (2013.01); *A61L 29/06* (2013.01); *A61L 29/14* (2013.01); *A61L 31/06* (2013.01); *A61L 31/14* (2013.01); *A61M 25/005* (2013.01); *A61M 25/0054* (2013.01); *A61M 25/008* (2013.01); *A61M 25/0009* (2013.01); *A61M 25/0045* (2013.01); *A61M 25/0053* (2013.01)

(58) Field of Classification Search
CPC .......... A61M 25/0009; A61M 25/0012; A61M 25/0045; A61M 25/005; A61M 25/0053; A61M 25/0054; A61M 25/008; A61M 2025/0046; A61M 2025/0047; A61M 2025/0048; A61M 2025/0062; A61M 2025/0064
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |

(Continued)

FOREIGN PATENT DOCUMENTS

| | | | |
|---|---|---|---|
| AU | 723040 B2 | 12/1997 | |
| AU | 733966 B2 | 4/1998 | |

(Continued)

*Primary Examiner* — Robert Lynch
(74) *Attorney, Agent, or Firm* — Seager, Tufte & Wickhem LLP

(57) ABSTRACT

A medical device may include an elongated shaft. The elongated shaft may further include a reinforcement member having a first portion and a second portion. The first portion may include a polymer having a first degree of crystallinity. The second portion may include a second degree of crystallinity different than the polymer of the first portion.

18 Claims, 9 Drawing Sheets

(56) References Cited

U.S. PATENT DOCUMENTS

| | | |
|---|---|---|
| 2,441,166 A | 5/1948 | Raspet |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,523 A | 8/1967 | Rieser |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,318,402 A | 3/1982 | Vaillancourt |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,547,192 A | 10/1985 | Brodsky et al. |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gurs |
| 4,665,906 A | 5/1987 | Jervis |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa et al. |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horezewski et al. |
| 4,934,380 A | 6/1990 | De Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Towne et al. |
| 5,063,935 A | 11/1991 | Gambale |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,195,984 A | 3/1993 | Schatz |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,316,706 A * | 5/1994 | Muni ............... A61M 25/0009 264/209.1 |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,358,493 A | 10/1994 | Schweich et al. |
| 5,365,942 A | 11/1994 | Shank |
| 5,365,943 A | 11/1994 | Jansen |
| 5,368,564 A | 11/1994 | Savage |
| 5,376,084 A | 12/1994 | Bacich et al. |
| 5,381,782 A | 1/1995 | Delarama et al. |
| 5,406,960 A | 4/1995 | Corso, Jr. |
| 5,411,476 A | 5/1995 | Abrams et al. |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,480,382 A | 1/1996 | Hammerslag et al. |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |

(56) References Cited

U.S. PATENT DOCUMENTS

| | | |
|---|---|---|
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk et al. |
| 5,676,697 A | 10/1997 | McDonald |
| 5,682,894 A | 11/1997 | Orr et al. |
| 5,690,120 A | 11/1997 | Jacobsen et al. |
| 5,702,373 A | 12/1997 | Samson |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Quin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,923 A | 11/1998 | Mayer |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | Van Minden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock et al. |
| 5,904,657 A | 5/1999 | Unsworth et al. |
| 5,906,618 A | 5/1999 | Larson, III et al. |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone et al. |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,971,975 A | 10/1999 | Mills et al. |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 * | 4/2002 | Jansen ............... A61M 25/005 600/435 |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen et al. |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 | 6/2003 | Jacobsen et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,682,493 B2 | 1/2004 | Mirigian |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |

(56) References Cited

U.S. PATENT DOCUMENTS

| | | |
|---|---|---|
| 7,074,197 B2 | 7/2006 | Reynolds et al. |
| 7,540,865 B2 | 6/2009 | Griffin et al. |
| 7,914,466 B2 | 3/2011 | Davis et al. |
| 7,955,272 B2 | 6/2011 | Rooney et al. |
| 8,048,004 B2 | 11/2011 | Davis et al. |
| 8,048,060 B2 | 11/2011 | Griffin et al. |
| 8,182,465 B2 | 5/2012 | Griffin et al. |
| 2002/0013540 A1 | 1/2002 | Jacobsen et al. |
| 2002/0019599 A1 | 2/2002 | Rooney et al. |
| 2003/0009208 A1 | 1/2003 | Snyder et al. |
| 2003/0060732 A1 | 3/2003 | Jacobsen et al. |
| 2003/0069520 A1 | 4/2003 | Skujins et al. |
| 2003/0069521 A1 | 4/2003 | Reynolds et al. |
| 2003/0069522 A1 | 4/2003 | Jacobsen et al. |
| 2004/0167437 A1 | 8/2004 | Sharrow et al. |
| 2004/0181174 A2 | 9/2004 | Davis et al. |
| 2004/0181176 A1 | 9/2004 | Jafari et al. |
| 2006/0004168 A1* | 1/2006 | Greer ............... A61L 27/16 526/352 |
| 2006/0189896 A1 | 8/2006 | Davis et al. |
| 2006/0264904 A1 | 11/2006 | Kerby et al. |
| 2007/0270779 A1* | 11/2007 | Jacobs ............... A61M 25/0045 604/525 |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0077119 A1 | 3/2008 | Snyder et al. |
| 2012/0041094 A1* | 2/2012 | Oral ............... A61L 27/16 522/75 |

FOREIGN PATENT DOCUMENTS

| | | |
|---|---|---|
| BR | 9712829 A | 1/2000 |
| CA | 2266685 C | 5/2006 |
| CN | 1230914 A | 10/1999 |
| DE | 2539191 A | 3/1976 |
| DE | 3621967 A1 | 1/1988 |
| EP | 0045931 A2 | 2/1982 |
| EP | 0069522 A1 | 1/1983 |
| EP | 0087933 A1 | 9/1983 |
| EP | 0111044 A2 | 6/1984 |
| EP | 0181174 A2 | 5/1986 |
| EP | 0377453 A1 | 7/1990 |
| EP | 0521595 A2 | 1/1993 |
| EP | 0565065 A1 | 10/1993 |
| EP | 0608853 A2 | 8/1994 |
| EP | 0778038 A2 | 6/1997 |
| EP | 0778039 A1 | 6/1997 |
| EP | 0778040 A2 | 6/1997 |
| EP | 0790066 A2 | 8/1997 |
| EP | 0807446 A2 | 11/1997 |
| EP | 0812599 A2 | 12/1997 |
| EP | 0865772 A1 | 9/1998 |
| EP | 0865773 A1 | 9/1998 |
| EP | 0917885 A1 | 5/1999 |
| EP | 0937481 A1 | 8/1999 |
| EP | 0935947 B1 | 12/2004 |
| EP | 0934141 B1 | 11/2005 |
| GB | 2214354 A | 8/1989 |
| GB | 2257269 A | 1/1993 |
| JP | 588522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 63093516 | 4/1988 |
| JP | 63181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 3122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5506806 | 10/1993 |
| JP | 5309519 | 11/1993 |
| JP | 5507857 | 11/1993 |
| JP | 6501179 | 2/1994 |
| JP | 631749 | 4/1994 |
| JP | 6169996 | 6/1994 |
| JP | 663224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8229888 | 7/1996 |
| JP | 8509141 | 10/1996 |
| JP | 8317988 | 12/1996 |
| JP | 9000164 | 4/1997 |
| JP | 9276413 | 10/1997 |
| JP | 9294813 | 11/1997 |
| JP | 10118193 | 5/1998 |
| JP | 10305039 | 11/1998 |
| JP | 10328191 | 12/1998 |
| JP | 11226131 | 8/1999 |
| JP | 11267224 | 10/1999 |
| JP | 2000197704 | 7/2000 |
| JP | 2000510722 | 8/2000 |
| JP | 2000511083 | 8/2000 |
| JP | 2001500808 A | 1/2001 |
| JP | 2002529137 A | 9/2002 |
| JP | 2002542901 A | 12/2002 |
| JP | 2002543896 A | 12/2002 |
| JP | 2003517893 A | 6/2003 |
| JP | 3649604 | 2/2005 |
| JP | 2005534407 A | 11/2005 |
| SU | 712908 | 8/1980 |
| SU | 758421 | 8/1980 |
| SU | 1529365 A1 | 12/1989 |
| WO | 9002520 A1 | 3/1990 |
| WO | 9113364 A2 | 9/1991 |
| WO | 9204072 A1 | 3/1992 |
| WO | 9304722 A2 | 3/1992 |
| WO | 9207619 A1 | 5/1992 |
| WO | 9311313 A1 | 6/1993 |
| WO | 9524263 A1 | 9/1995 |
| WO | 9619255 A1 | 6/1996 |
| WO | 9710022 A2 | 3/1997 |
| WO | 9725914 A1 | 7/1997 |
| WO | 9743949 A1 | 11/1997 |
| WO | 9744083 A1 | 11/1997 |
| WO | 9744086 A1 | 11/1997 |
| WO | 9810694 A3 | 7/1998 |
| WO | 9904847 A1 | 2/1999 |
| WO | 9911313 A1 | 3/1999 |
| WO | 0027303 A2 | 5/2000 |
| WO | 0030710 A1 | 6/2000 |
| WO | 0048645 A2 | 8/2000 |
| WO | 0057943 A1 | 10/2000 |
| WO | 0066199 A1 | 11/2000 |
| WO | 0072907 A1 | 12/2000 |

(56) References Cited

FOREIGN PATENT DOCUMENTS

| | | | |
|---|---|---|---|
| WO | 0128620 | A1 | 4/2001 |
| WO | 0136034 | A2 | 5/2001 |
| WO | 0145773 | A1 | 6/2001 |
| WO | 0145912 | A1 | 6/2001 |
| WO | 0067845 | A1 | 11/2001 |
| WO | 0193920 | A2 | 12/2001 |
| WO | 0213682 | A1 | 2/2002 |
| WO | 02062540 | A2 | 8/2002 |
| WO | 03004086 | A2 | 1/2003 |
| WO | 03008148 | A2 | 1/2003 |
| WO | 2004012804 | A2 | 2/2004 |
| WO | 2004047899 | A1 | 6/2004 |
| WO | 2012116337 | A1 | 8/2012 |

* cited by examiner

CATHETERS AND CATHETER SHAFTS

CROSS-REFERENCE TO RELATED APPLICATION

This application claims priority under 35 U.S.C. § 119 to U.S. Provisional Application Ser. No. 61/978,551, filed Apr. 11, 2014, the entirety of which is incorporated herein by reference.

TECHNICAL FIELD

The present disclosure pertains generally, but not by way of limitation, to medical devices and methods for manufacturing medical devices. More particularly, the present disclosure pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, and manufacturing method alternatives for medical devices. In a first example, a medical device comprises an elongated shaft including a reinforcement member, the reinforcement member including a first portion and a second portion; and the first portion having a first degree of polymeric crystallinity and the second portion having a second degree of polymeric crystallinity different than the first degree of polymeric crystallinity.

Alternatively or additionally to the above example, in another example, the elongated shaft includes an inner layer and an outer layer.

Alternatively or additionally to any of the examples above, in another example, the inner layer includes polytetrafluoroethylene.

Alternatively or additionally to any of the examples above, in another example, the inner layer includes fluorinated ethylene propylene.

Alternatively or additionally to any of the examples above, in another example, the outer layer includes polyether block amide.

Alternatively or additionally to any of the examples above, in another example, the outer layer includes a blend of polyether block amide and polyurethane.

Alternatively or additionally to any of the examples above, in another example, the reinforcement member is disposed between the inner layer and the outer layer.

Alternatively or additionally to any of the examples above, in another example, the reinforcement member includes a polymeric braid.

Alternatively or additionally to any of the examples above, in another example, the reinforcement member includes a polymeric coil.

Alternatively or additionally to any of the examples above, in another example, the reinforcement member includes ultra-high molecular weight polyethylene braid.

Alternatively or additionally to any of the examples above, in another example, the first portion having a first degree of polymeric crystallinity and the second portion having a second degree of polymeric crystallinity lower than the first degree of polymeric crystallinity.

Alternatively or additionally to any of the examples above, in another example, the reinforcement member comprising at least two materials.

Alternatively or additionally to any of the examples above, in another example, the reinforcement member is at least partially embedded within the outer layer of the elongated shaft.

Alternatively or additionally to any of the examples above, in another example, the elongated shaft including the reinforcement member and an axial reinforcement member.

Furthermore, another example includes a method for manufacturing a medical device, the method comprising: forming an elongated shaft, wherein forming the elongated shaft includes a reinforcement layer having a first portion and a second portion; heating the elongated shaft; and wherein heating the elongated shaft causes the first portion to have a first degree of polymeric crystallinity and the second portion to have a second degree of polymeric crystallinity different than the first degree of polymeric crystallinity.

Alternatively or additionally to any of the examples above, another example includes, forming the elongated shaft comprises disposing the reinforcement member between an inner layer and an outer layer.

Alternatively or additionally to any of the examples above, another example includes, forming the elongated shaft comprises the reinforcement member including a polymeric braid.

Alternatively or additionally to any of the examples above, another example includes forming the elongated shaft comprises the reinforcement member including ultra-high molecular weight polyethylene braid.

Alternatively or additionally to any of the examples above, another example includes heating the elongated shaft comprises the first portion having a first degree of polymeric crystallinity and the second portion having a second degree of polymeric crystallinity lower than the first degree of polymeric crystallinity.

Alternatively or additionally to any of the examples above, another example includes forming the elongated shaft comprises the reinforcement member comprising at least two materials.

Alternatively or additionally to any of the examples above, another example includes forming the elongated shaft comprises the elongated shaft including the reinforcement member and an axial reinforcement member.

Furthermore, another example includes a medical device, comprising: an elongated shaft including a reinforcement member; the reinforcement member comprising at least two materials and the reinforcement member including a first portion and a second portion; and the first portion having a first degree of polymeric crystallinity and the second portion having a second degree of polymeric crystallinity different than the first degree of polymeric crystallinity.

Furthermore, another example includes a medical device, comprising: an elongated shaft including a reinforcement member and an axial reinforcement member, the reinforcement member including a first portion and a second portion; and the first portion having a first degree of polymeric crystallinity and the second portion having a second degree of polymeric crystallinity different than the first degree of polymeric crystallinity.

Furthermore, another example includes a medical device, comprising: an elongated shaft including an axial reinforcement member, the axial reinforcement member including a first portion and a second portion; and the first portion having a first degree of polymeric crystallinity and the second portion having a second degree of polymeric crystallinity different than the first degree of polymeric crystallinity.

Furthermore, another example includes a medical device, comprising: an elongated shaft including an inner polymeric layer and an outer polymeric layer, a reinforcement member disposed over the inner polymeric layer and at least partially embedded within the outer polymeric layer, the outer polymeric layer disposed over the inner polymeric layer and the reinforcement member, the reinforcement member including ultra-high molecular weight polyethylene braid having a first portion and a second portion; and the first portion having a first degree of polymeric crystallinity and the second portion having a second degree of polymeric crystallinity different than the first degree of polymeric crystallinity.

The above summary of some examples and embodiments is not intended to describe each disclosed embodiment or every implementation of the present disclosure. The Brief Description of the Drawings, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings, in which.

Figure 1:
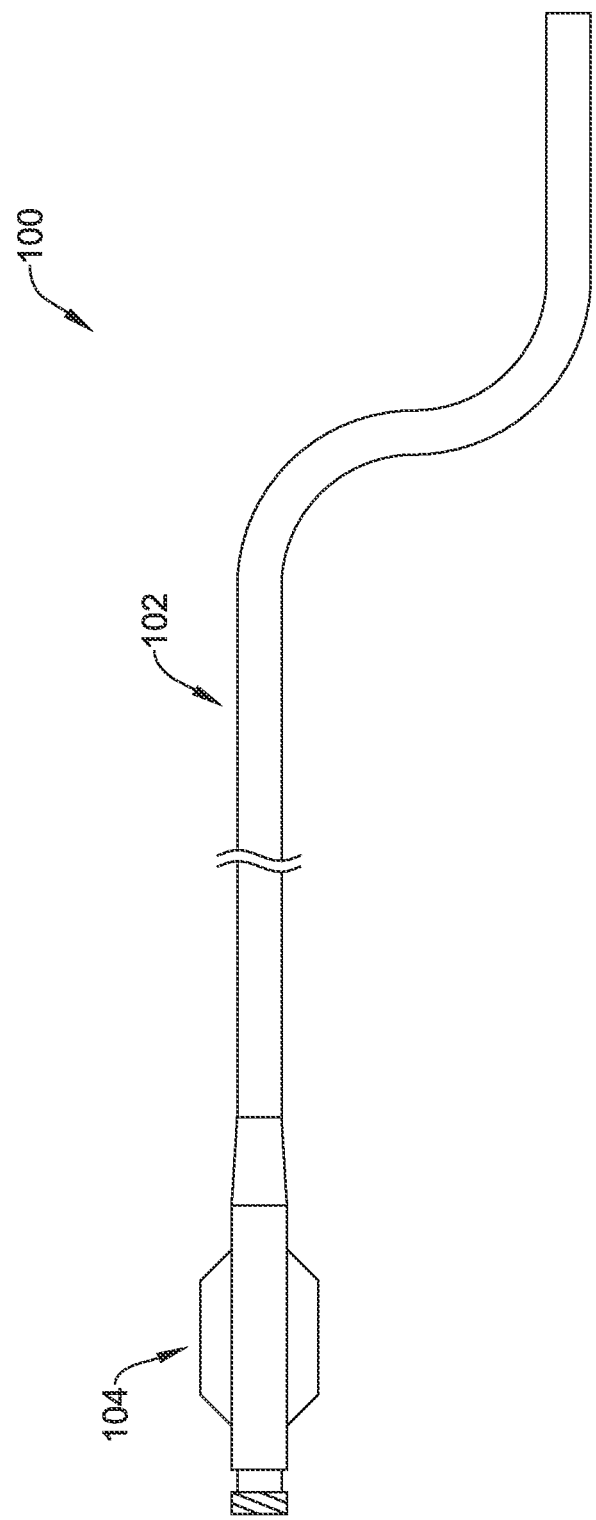
FIG. 1 is a perspective view of an exemplary medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

The following detailed description should be read with reference to the drawings, in which similar elements in different drawings are identified with the same reference numbers. The drawings, which are not necessarily to scale, depict illustrative embodiments and are not intended to limit the scope of the disclosure.

The present disclosure pertains to medical devices made with materials having variable crystallinity and methods of manufacturing medical devices with materials having variable crystallinity. Crystallinity refers to the degree of structural order in a solid material. In a crystalline material, such as a crystalline polymer, atoms and molecules are arranged in a regular periodic manner. The degree of crystallinity of a material affects its physical properties such as stiffness, density, transparency or the like. For example, the stiffness of a material may change with the degree of crystallinity of the material. If a first material has a degree of crystallinity more than the degree of crystallinity of a second material, then the first material may be stiffer than the second material. A medical device including the first material disposed at a first portion and the second material disposed at a second portion may have a variable stiffness, e.g., the first portion of the medical device may be stiffer than the second portion, which may be desirable in various applications.

For example, many medical procedures require tracking catheters into tortuous intracorporeal cavities, such as blood vessels. Catheters need variable stiffness along their length to exhibit desirable properties such as maneuverability through tortuous paths, kink resistance, atraumatic distal end, and the like. For example, a catheter can advantageously include a proximal portion having sufficient stiffness to allow an operator to push and torque the catheter, from a proximal end, to maneuver the catheter in a patient's body without kinking. In addition, the catheter can include a distal portion with sufficient flexibility to be advanced into tortuous anatomy. Further, the distal tip of the catheter can be sufficiently flexible to prevent trauma to surrounding tissue upon contact.

In some embodiments, a method of manufacturing medical devices, such as catheters, with a material having variable stiffness may include changing the degree of crystallinity of the material disposed within the medical device on different portions of the medical device. Depending on the initial crystallinity and method of cooling of a material, the degree of crystallinity of the material can be changed by a number of methods, for example, heating certain crystalline polymeric materials such as polyethelene, nylon, PEEK, or the like in their respective crystalline melt range reduces the degree of crystallinity of the polymeric materials. Thus, heating a portion of the medical device to a suitable temperature range may make the material disposed within that portion less stiff compared to other unaltered portions of the medical device.

The present disclosure describes various example embodiments of a catheter having at least one reinforcement member made of a material that may be configured with a variable range of crystallinity. For example, in some embodiments, a catheter may have two portions, a first portion and a second portion. The second portion of the catheter may be heated to reduce the degree of crystallinity of the reinforcement member in the second portion to make the reinforcement member less stiff in the second portion as compared to the first portion. Consequently, the second portion of the catheter may become less stiff than the first portion of the catheter. Embodiments also include catheters, or other medical devices, having more than two portions. However, such a reinforcement member with variable stiffness can be included in many other medical devices such as balloon catheters, stent delivery catheters, guidewires, implants, or the like to vary their stiffness at a desired location.

FIG. 1 is a perspective view of an exemplary medical device. In FIG. 1, a perspective view of a catheter 100 is shown. The catheter 100 may include an elongated shaft 102 and a hub assembly 104 attached to the proximal end of the elongated shaft 102. The elongated shaft 102 may have one or more lumens (not shown) extending through the length of the elongated shaft 102, for example, a central lumen 206 (shown in FIG. 2). The lumen(s) may be in communication with one or more ports on the hub assembly 104 to insert or remove additional medical devices, fluids, or the like (not shown) into the lumen(s) of the elongated shaft 102 for transporting to target locations within the patient's body. Some examples of additional medical devices include, but are not limited to, balloon catheters, stent delivery catheters, snares, baskets or the like. Further, the catheter 100 may be configured with a suitable handle, actuators, or the like to allow an operator to manipulate the catheter 100 from the proximal end of the elongated shaft 102. The operator may push or torque the catheter 100 from the proximal end of the elongated shaft 102 to maneuver the elongated shaft 102 in the patient's body.

Figure 2:
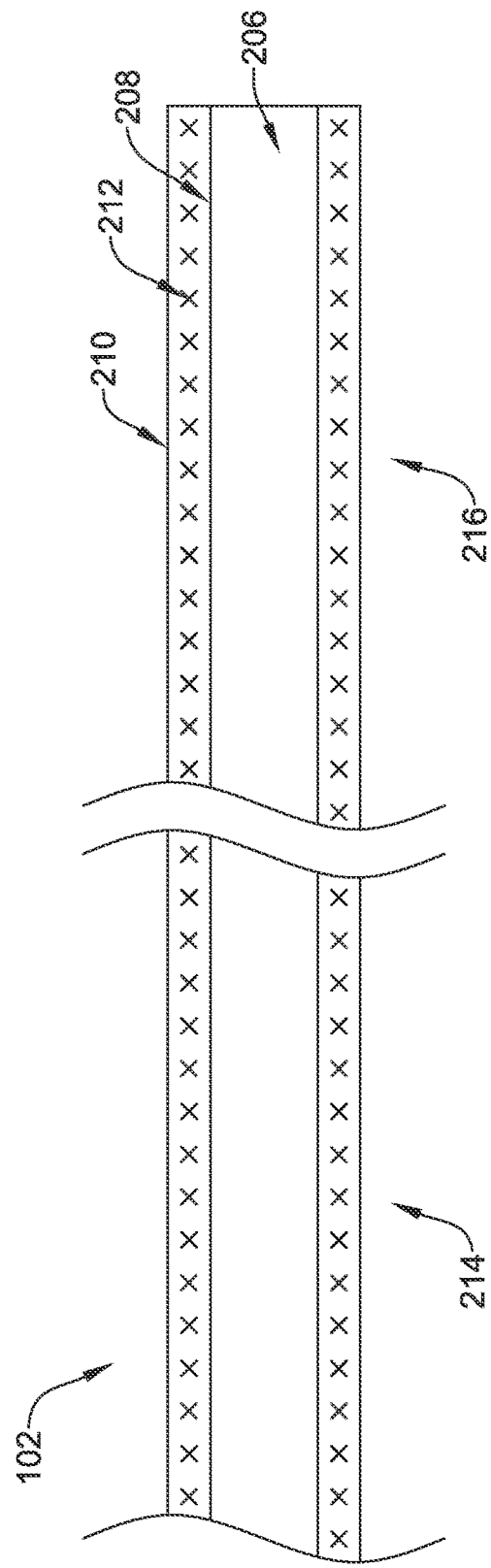
FIG. 2 is a cross-sectional view of an exemplary elongated shaft of the medical device of FIG. 1.

FIG. 2 is a cross-sectional view of an exemplary elongated shaft of the medical device of FIG. 1. FIG. 2 shows a cross-sectional view of the elongated shaft 102 of catheter 100 of FIG. 1. As discussed, the elongated shaft 102 may include a central lumen 206 for inserting additional medical devices through the elongated shaft 102. The elongated shaft 102 may include one or more layers of material. The elongated shaft 102 may include three layers of material including an inner layer 208, an outer layer 210, and a reinforcement member 212 disposed between the inner layer 208 and the outer layer 210.

The inner layer 208 may provide a smooth frictionless surface along the lumen 206 to dispose the additional medical devices in the elongated shaft 102. The outer layer 210 may provide a frictionless biocompatible outer surface to the elongated shaft 102 to maneuver the elongated shaft in a patient's body without damaging surrounding tissue. In some embodiments, the inner layer 208 and the outer layer 210 may be made of the same or different material. For example, the inner layer 208 may include materials, such as polytetrafluroethylene (PTFE), fluorinated ethylene propylene (FEP) or the like or a blend of such materials. The outer layer 210 may include materials such as polyether block amide (PBA), polyurethane or the like or a blend of such materials.

The reinforcement member 212 may include wires, fibers, ribbons, or the like arranged in various ways to provide sufficient stiffness to the catheter 100. For example, as shown, the reinforcement member 212 may have a monofilament or multi-filament braided structure. The reinforcement member 212 may be an axial or a biaxial braid with a suitable reinforcing braid pitch and angle. Other embodiments of the reinforcement member 212 may include a coil, sheath, foam, or the like.

The reinforcement member 212 may have a variable crystallinity along the length of the elongated shaft 102 and may provide variable stiffness to the elongated shaft 102. In some embodiments, the reinforcement member 212 may have multiple portions, each having a different crystallinity, along the length of the elongated shaft 102. For example, as shown, the reinforcement member 212 may include a first portion 214 (a proximal end portion) and a second portion 216 (a distal end portion) along the length of the catheter 100. The first portion 214 may include a material of a first degree of crystallinity and the second portion 216 may include a material of a second degree of crystallinity different than the material of the first portion 214. In some embodiments, the first portion 214 and the second portion 216 may be made of polymers with different crystallinity. In some other embodiments, the reinforcement member 212 may be made up of a single polymeric material, and the crystallinity of the material in the first portion 214 or the second portion 216 may be modified by heating or other suitable methods.

In at least some embodiments, the reinforcement member 212 may be made of one or more crystalline polymer or polymeric materials such as an ultra-high molecular weight polyethelene (UHMWPE), polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyether-ester, ether or ester based copolymers (for example, butylene/poly(alkylene ether) phthalate and/or other polyester elastomers), polyamide, elastomeric polyamides, block polyamide/ethers, polyether block amide (PEBA), ethylene vinyl acetate copolymers (EVA), silicones, polyethylene (PE), Marlex high-density polyethylene, Marlex low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), liquid crystal polymers (LSP), polyaramid polymetaphenylene isopthalamide, polyetherimide (PEI), polyphenylene sulfide (PPS), polyphenylene oxide (PPO), poly paraphenylene terephthalamide, polysulfone, nylon, nylon-12, perfluoro(propyl vinyl ether) (PFA), ethylene vinyl alcohol, polyolefin, polystyrene, epoxy, polyvinylidene chloride (PVdC), poly(styrene-b-isobutylene-b-styrene), polycarbonate copolymers, ionomers, biocompatible polymers, other suitable materials, or mixtures, combinations, copolymers thereof, polymer/metal composites, and the like.

Referring to FIGS. 1 and 2, in an exemplary method of use, an operator may insert the distal end of the catheter 100 in a patient's body through an incision or a natural anatomical opening. The operator may then push the elongated shaft 102 through paths in the patient's body to a target location. While traversing the elongated shaft 102 in the patient's body, the flexible distal end portion of the elongated shaft 102 (less stiff than the proximal portion) having the second portion 216 of the reinforcement member 212 may assist the operator to move the elongated shaft 102 through various twists and turns in the patient's body. In addition, the flexible second portion 216 (distal end portion) of the elongated shaft 102 may form an atraumatic tip which may prevent any trauma to the patient's tissue while traversing the elongated shaft 102 to the target location. Further, the stiff first portion 214 (proximal portion) of the elongated shaft 102 (more stiff than the distal portion) having the first portion 214 of the reinforcement member 212 may assist the operator to push the elongated shaft 102 from the proximal end of the elongated shaft 102. In addition, the stiff proximal portion prevents kinking of the elongated shaft 102 in the patient's body. After traversing the elongated shaft 102 to the target location, the operator may insert suitable therapeutic or diagnostic tools in the central lumen 206, through the hub assembly 104, to conduct the required medical procedure on the target tissue. Then, the operator may retract the elongated shaft 102 out of the patient's body.

Figure 3:
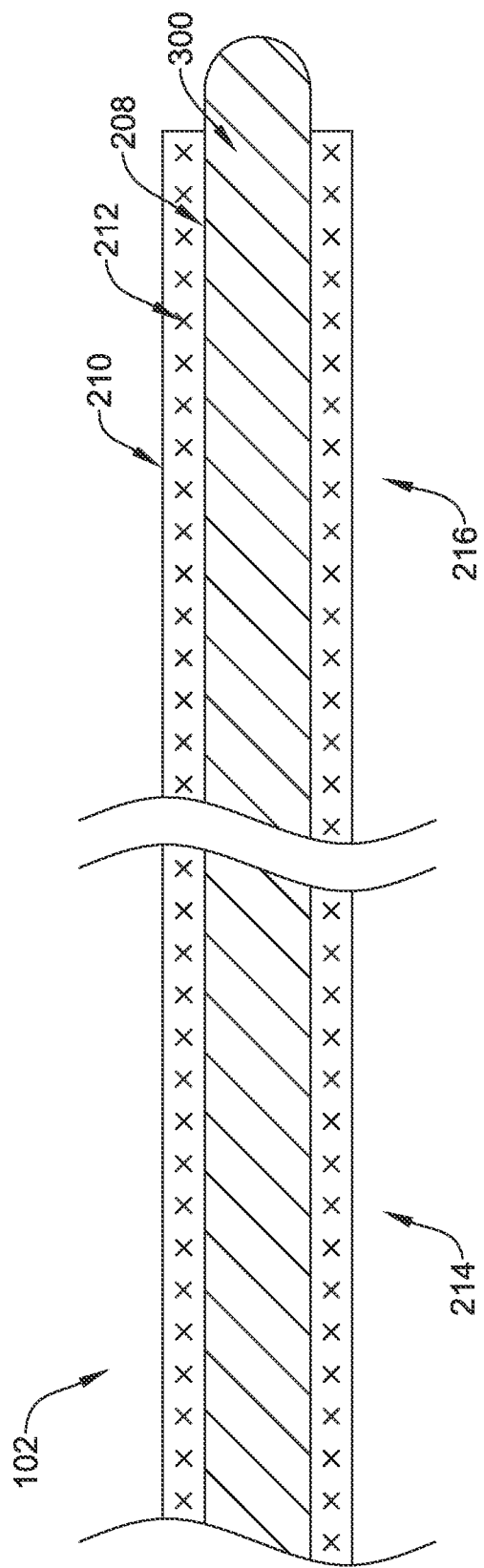
FIGS. 3-5 are cross-sectional views of the method for manufacturing the medical device of FIG. 1.
Figure 4:
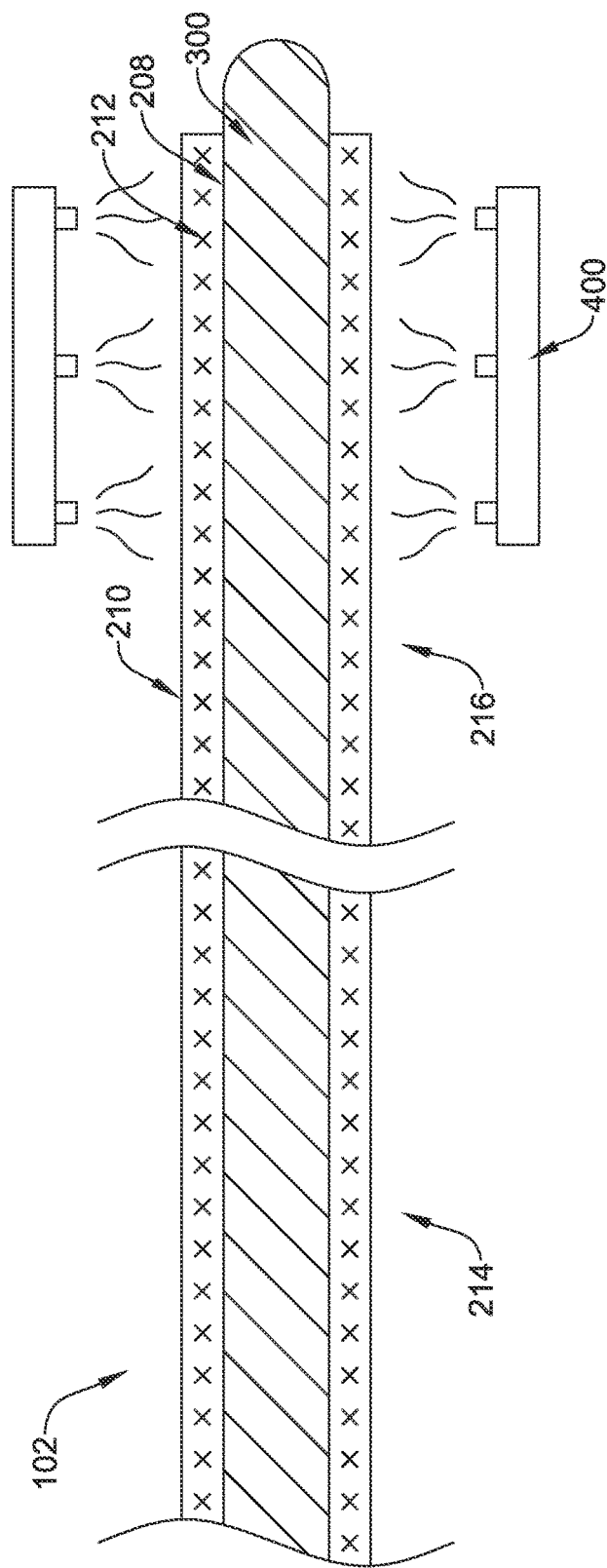
Figure 5:
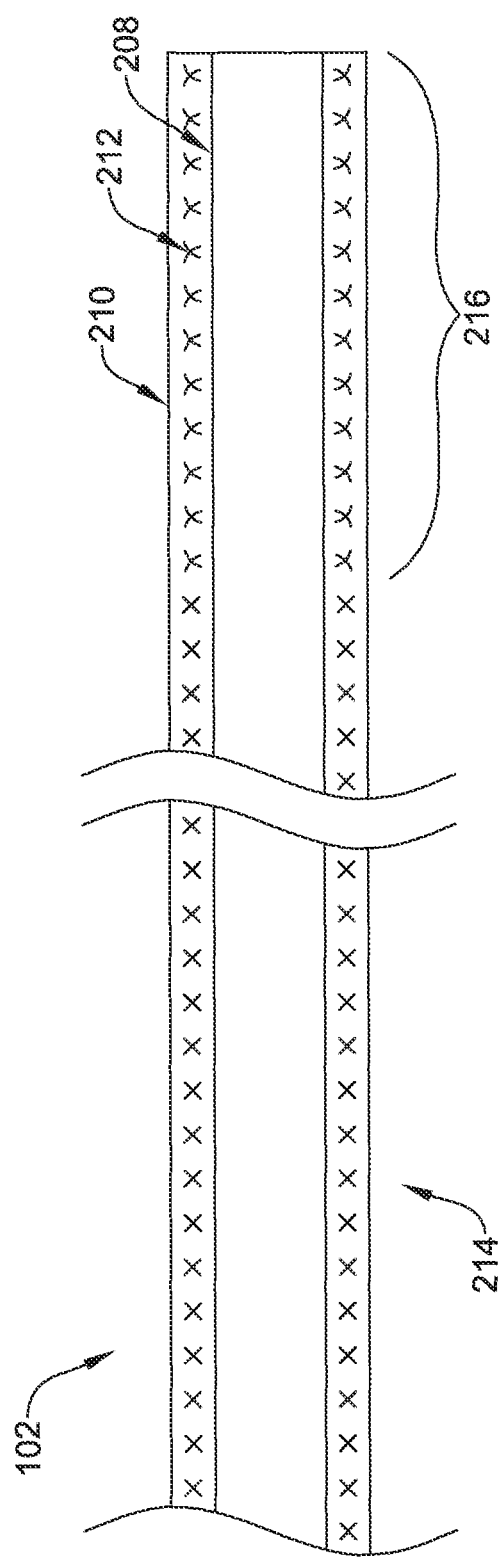

FIGS. 3-5 are cross-sectional views of the method for manufacturing the medical device of FIG. 1, for example the catheter 100. FIG. 3 is a cross-sectional view of the elongated shaft 102 disposed along a mandrel 300. The mandrel may vary in size, depending on the intervention. For example, the mandrel may be a silver coated copper core, acetal, stainless steel, nickel-titanium alloy or other suitable mandrel with an outer diameter in the range of about 0.01 to 0.05 inches (0.03 to 0.13 centimeters), or about 0.02 to 0.04 inches (0.05 to 0.10 centimeters), or about 0.022 to 0.027 inches (0.056 to 0.069 centimeters). As shown, the reinforcement member 212 is placed between the inner layer 208 and the outer layer 210. In some embodiments, the inner layer 208 may be extruded on the mandrel 300. A resin of suitable polymeric materials such as, but not limited to polytetrafluroethylene (PTFE), or fluorinated ethylene propylene (FEP) may be extruded over the mandrel 300 to form the inner layer 208. The mandrel 300 may have a shape suitable to give a desired shape to the inner layer 208. In other embodiments, outer layer 210 may be disposed along the outer surface of inner layer 208 and reinforcement member 212 may be disposed along the outer surface of outer layer 210. The process for disposing layers 208/210/212 onto the mandrel may include an extrusion process. When using an extrusion process, the assembly may be subjected to extrusion temperatures in the range of about 100 to 200° C., or about 120 to 190° C., or about 140 to 170° C. Under such conditions, reinforcement member 212 may become embedded and/or at least partially embedded within outer layer 210. For example, at least a portion of outer layer 210 may be disposed radially outward of the outer surface of reinforcement layer 212. In some instances, reinforcement member 212 may become disposed at or near the inner surface of outer layer 210 so that reinforcement member 212 is essentially positioned between the inner layer 208 and outer layer 210. In some of these and in other embodiments, portions of outer layer 210 may be interlocked with or otherwise disposed within the interstices of reinforcement member 212. This may form or define a "composite layer" that includes both the material of reinforcement member 212 and the material of outer layer 210. In other embodiments, reinforcement member 212 may become embedded and/or at least partially embedded within inner layer 208. In some instances, reinforcement member 212 may become disposed at or near the inner surface of outer layer 210 so that reinforcement member 212 is essentially positioned between the inner layer 208 and outer layer 210 and embedded within the inner layer 208 of the elongated shaft 102.

The process for manufacturing elongated shaft 102 (e.g., the extrusion process) may allow for relatively thin elongated shafts 102 to be manufactured. For example, elongated shaft 102 may have a wall thickness as low as about 0.0005 to 0.0010 inches (0.003 to 0.0025 centimeters), or about 0.001 to 0.002 inches (0.003 to 0.005 centimeters), or about 0.0015 inches (0.0038 centimeters). In general, the process may allow for elongated shafts 102 to be manufactured having relatively larger inner diameters while still maintaining relatively small outer diameters. The process may also result in relatively strong elongated shafts 102. For example, elongated shaft 102 may have a tensile strength capable of withstanding forces up to about 10-20 foot-pounds (14 to 27 joules), or up to about 12-18 foot-pounds (16 to 24 joules), or up to about 16 foot-pounds (22 joules). For example, elongated shaft 102 may be capable of withstanding pressures exceeding 800 psi (5516 kilopascal, or exceeding 1000 psi (6895 kilopascal), or exceeding 1200 psi (8274 kilopascal). The presence of reinforcement member 212 may also provide elongated shaft 102 with enhanced cut resistance, tear resistance, kink resistance, etc. These features may be further enhanced when reinforcement member 212 is positioned at or near the outer surface of elongated shaft 102.

The reinforcement member 212 may be placed over the inner layer 208 forming a reinforcing layer to provide stiffness to the elongated shaft 102. The reinforcement member 212 may be formed by disposing a braid of a crystalline polymeric material over the inner layer 208. The reinforcement member 212 may be formed as an axial or a biaxial braid of a suitable crystalline material with a suitable pitch angle to impart strength to the reinforcement member 212.

Then, a resin of suitable polymeric material, such as, but not limited to, polyether block amide (PBA), polyurethane or a blend of the two materials may be extruded over the reinforcement member 212 and the inner layer 208 to form the outer layer 210. The outer layer 210 may fill the voids or gaps in the braid such that the reinforcement member 212 may at least partially embed within the outer layer 210 forming a sandwich like structure. In some embodiments, the outer layer 210 may fully cover the reinforcement member 212 so as to provide a smooth surface for contact with surrounding tissue. In some other embodiments, the outer layer 210 may partially cover the reinforcement member 212 such that a portion of the reinforcement member 212 is exposed to the surrounding tissue.

FIG. 4 illustrates that the crystallinity of the second portion 216 of the elongated shaft 102 may be altered by heating. Once the elongated shaft 102 is formed or extruded, the second portion 216 may be heated by a heater 400, which can be a heating oven, hot air convection jets, lasers, or the like. The heater 400 may be adapted to heat the second portion 216 to a temperature in the crystalline melt range of the material of the reinforcement member 212. For example, the reinforcement member 212 may include a crystalline polymer braid such as an ultra-high molecular weight polyethylene (UHMWPE) braid. The heater 400 may heat the second portion 216 in crystalline melt range of ultra-high molecular weight polyethylene (UHMWPE), from 300° F. to 350° F. (149° C. to 177° C.). The degree of crystallinity of the second portion 216 may reduce in comparison to the degree of crystallinity of the first portion 214. The reduced degree of crystallinity of the second portion 216 may make the reinforcement member 212 less stiff in the second portion 216 in comparison to the first portion 214.

In some embodiments, the heater 400 may heat the second portion 216 with a gradual temperature gradient or ramp in the crystalline melt range of the material of the reinforcement member 212. For example, if the reinforcement member 212 is an ultra-high molecular weight polyethylene (UHMWPE) braid, the heater 400 may heat the second portion 216 in a gradually increasing temperature ramp ranging from 300° F. (149° C.) at the proximal end of the second portion 216 to 350° F. (177° C.) at the distal end of the second portion 216. As a consequence, the graded heating of the second portion 216 may create a gradually decreasing degree of crystallinity and stiffness in the second portion 216 from the proximal end to the distal end of the second portion 216. FIG. 5 illustrates the elongated shaft 102 after removal of the mandrel 300 and the heater 400. As a consequence of heating of the second portion 216, the elongated shaft 102 may have a variable stiffness along the length of elongated shaft 102.

Figure 6:
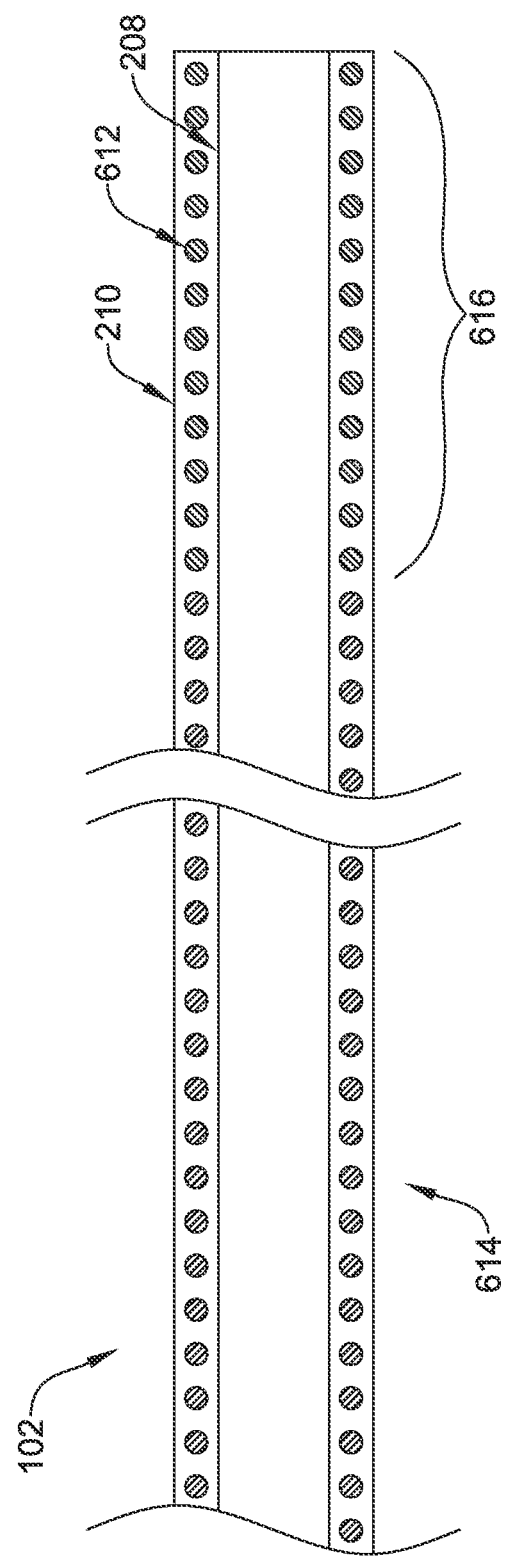
FIG. 6 is a cross-sectional view of another exemplary elongated shaft of the medical device of FIG. 1.

FIG. 6 is a cross-sectional view of another exemplary elongated shaft of the medical device of FIG. 1. FIG. 6 illustrates the elongated shaft 102 having a reinforcement member 612 structured as a mono or multi filament coil disposed between the inner layer 208 and the outer layer 210. Similar to the reinforcement member 212 shown in FIG. 2, the reinforcement member 612 may include a first portion 614 and a second portion 616. The material of the reinforcement member 612 may be a polymeric coil with some degree of crystallinity. The reinforcement member 612 may be manufactured using a method similar to the method described with respect to FIGS. 3-5. For example, the second portion 616 may be heated using a suitable heating mechanism to reduce the degree of crystallinity of the second portion 616 and consequently make the second portion 616 more flexible.

Figure 7:
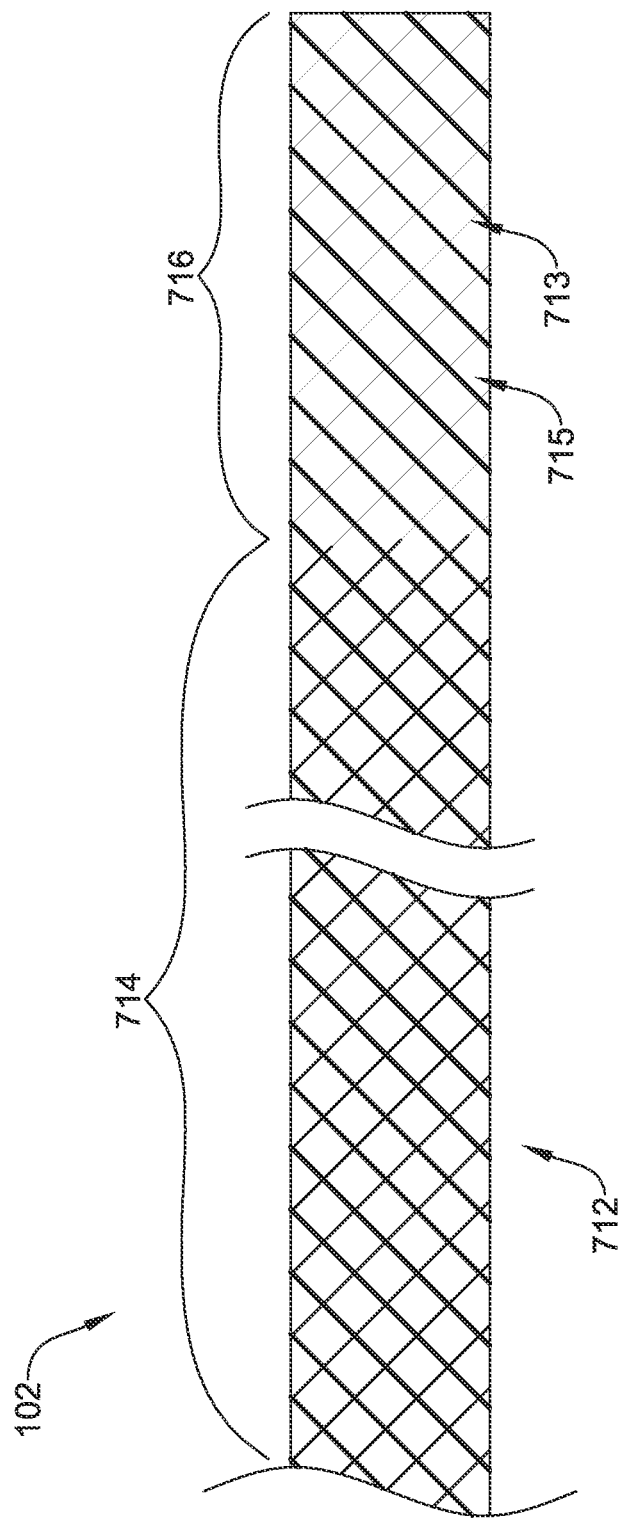
FIG. 7 is a schematic perspective view of another exemplary elongated shaft of the catheter medical device of FIG. 1.

FIG. 7 is a schematic perspective view of another exemplary elongated shaft of the catheter medical device of FIG. 1. As shown in FIG. 7, the reinforcement member may be made from composite materials. For example, a metal-polymer composite material may be used as a reinforcement member 712 in the elongated shaft 102. The reinforcement member 712 may include a composite material made of polymer fibers 713 and metal wires 715, which may be braided or in the form of a coil. The polymer fibers 713 may be made of a suitable crystalline polymer, such as ultra-high molecular weight polyethylene (UHMWPE) or the like. The metal wires 715 may be made of suitable metallic or alloy materials such as stainless steel, titanium, Nitinol™, or the like. The reinforcement member 712 may include a first portion 714 and a second portion 716. The reinforcement member 712 may be manufactured using a method similar to the method described with respect to FIGS. 3-5. The second portion 716 may be heated to reduce the crystallinity and stiffness of the polymer fibers 713, while the metal wires 715 may impart additional radial strength and kink resistance to the elongated shaft 102 stiffness of the polymer fibers 713 in the second portion 716.

Figure 8:
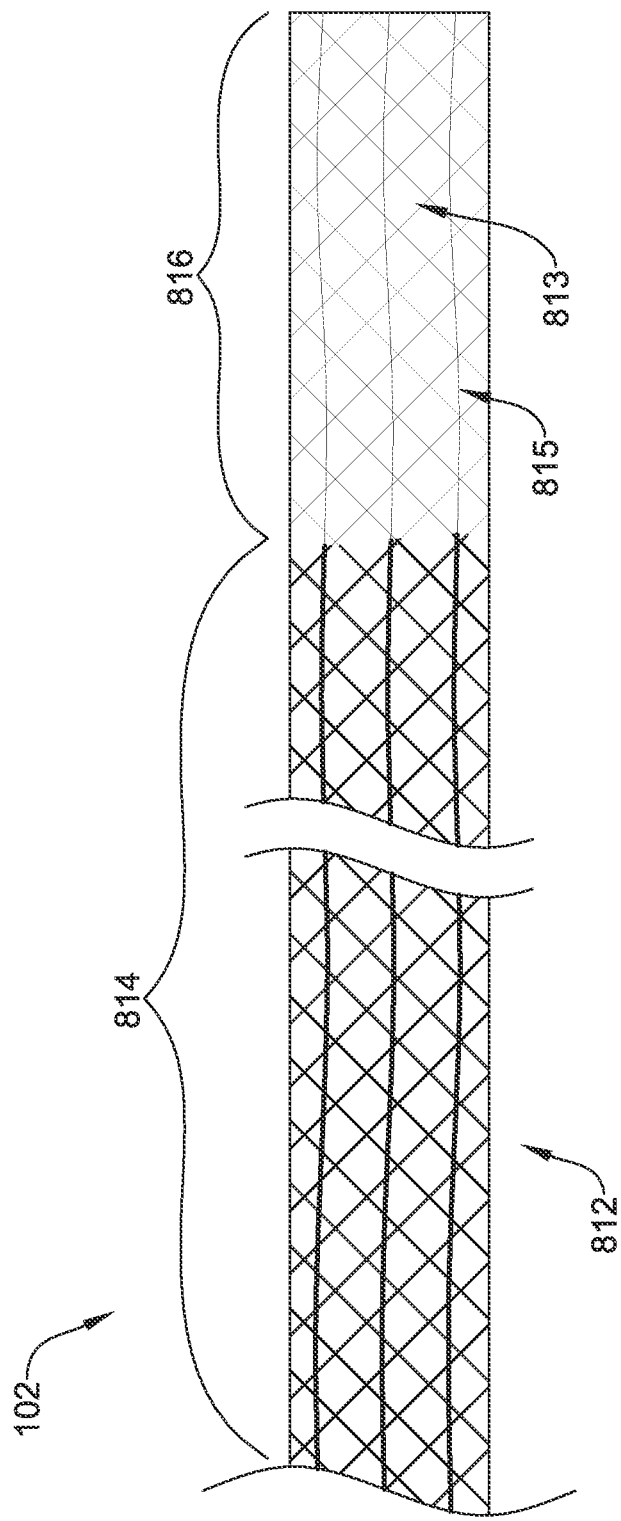
FIG. 8 is a schematic perspective view of another exemplary elongated shaft of the catheter medical device of FIG. 1.

FIG. 8 is a schematic perspective view of another exemplary elongated shaft of the catheter medical device of FIG. 1. As shown in FIG. 8, in some embodiments, the elongated shaft 102 may include one or more axial reinforcement members which may impart additional axial strength and kink resistance to the elongated shaft 102. For example, FIG. 8 illustrates the elongated shaft 102 with a composite reinforcement member 812 having a braid structure 813 and a plurality of axial reinforcement members 815, for example, mono or multifilament polymeric fibers extending axially along the length of the elongated shaft 102 disposed between the inner layer 208 and the outer layer 210 (e.g., shown in FIG. 2). As discussed, the axial reinforcement members 815 may impart additional stiffness and kink resistance to the elongated shaft 102. The reinforcement member 812 may include crystalline polymeric materials similar to the reinforcement member 212 (shown in FIG. 2). The reinforcement member 812 may include a first portion 814 and a second portion 816. The reinforcement member 812 having braid 813 and the axial reinforcement members 815 may be manufactured using a method similar to the method illustrated in FIGS. 3-5. The second portion 816 may be heated to reduce the crystallinity and stiffness of the polymer material of the reinforcement member 812.

Figure 9:
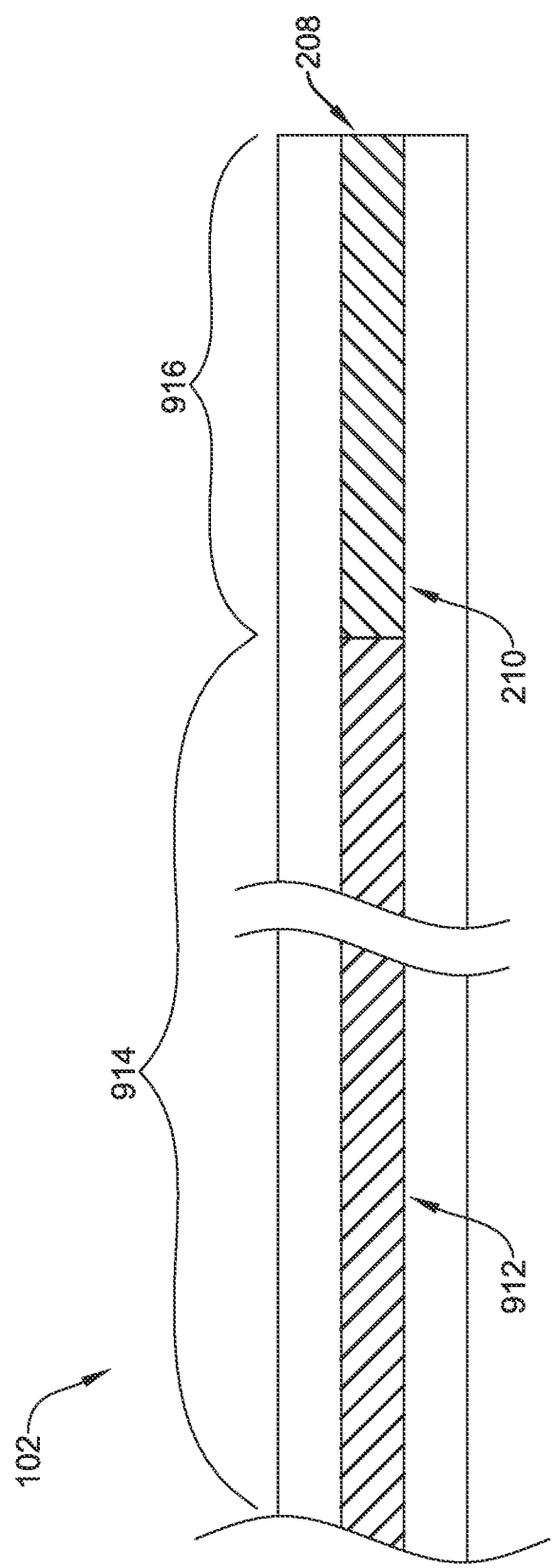
FIG. 9 is a schematic perspective view of another exemplary elongated shaft of the catheter medical device of FIG. 1.

FIG. 9 is a schematic perspective view of another exemplary elongated shaft of the catheter medical device of FIG. 1. As shown, in some embodiments, the elongated shaft 102 may include a reinforcement member with two or more materials having different degrees of crystallinity. For example, FIG. 9 depicts the elongated shaft 102 with a reinforcement member 912 having a first portion 914 made of a first material having a first degree of crystallinity and a second portion 916 made of a second material having a second degree of crystallinity. The material of the second portion 916 may have a degree of crystallinity lower than the degree of crystallinity of the first portion 914 to make the second portion 916 more flexible than the first portion 914. The reinforcement member 912 may be manufactured using a method similar to the method described in relation to FIGS. 3-5. After extrusion of the inner layer 208 on the mandrel 300, the first portion 914, which may be a braid of a suitable polymeric material such as ultra-high molecular weight polyethylene (UHMWPE), can be disposed over inner layer 208 at a proximal end portion of the elongated shaft 102. Then, the second portion 916, for example a braid of a suitable polymeric material having a degree of crystallinity less than the ultra-high molecular weight polyethylene (UHMWPE) braid, may be disposed over the inner layer 208 at a distal end portion of the elongated shaft 102. The first portion 914 and the second portion 916 may be made of one or more crystalline polymer or polymeric materials such as an ultra-high molecular weight polyethelene (UHMWPE), polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyetherester, ether or ester based copolymers (for example, butylene/poly(alkylene ether) phthalate and/or other polyester elastomers), polyamide, elastomeric polyamides, block polyamide/ethers, polyether block amide (PEBA), ethylene vinyl acetate copolymers (EVA), silicones, polyethylene (PE), Marlex high-density polyethylene, Marlex low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), liquid crystal polymers (LSP), polyaramid polymetaphenylene isopthalamide, polyetherimide (PEI), polyphenylene sulfide (PPS), polyphenylene oxide (PPO), poly paraphenylene terephthalamide, polysulfone, nylon, nylon-12, perfluoro(propyl vinyl ether) (PFA), ethylene vinyl alcohol, polyolefin, polystyrene, epoxy, polyvinylidene chloride (PVdC), poly(styrene-b-isobutylene-b-styrene), polycarbonates copolymers, ionomers, biocompatible polymers, other suitable materials, or mixtures, combinations, copolymers thereof, polymer/metal composites, and the like. The first portion 914 and the second portion 916 may be attached together through mechanical or chemical means, such as adhesives, filaments, or the like. Further, the outer layer 210 may be extruded over the reinforcement member 912 to form the elongated shaft 102.

The materials that can be used for the various components of catheter 100 (and/or other medical devices and/or catheter shafts disclosed herein) may include those commonly associated with medical devices. For simplicity purposes, the following discussion makes reference to elongated shaft 102 and other components of catheter 100. However, this is not intended to limit the devices and methods described herein, as the discussion may be applied to other similar tubular members and/or components of tubular members or devices disclosed herein.

Elongated shaft 102 and/or other components of catheter 100 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluorethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, utylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide, polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®), other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®), and the like); platinum enriched stainless steel; titanium; combinations thereof; and the like; or any other suitable material.

In at least some embodiments, portions or all of elongated shaft 102 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of catheter 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of catheter 100 to achieve the same result. In some embodiments, a degree of Magnetic Resonance Imaging (MRI) compatibility may be imparted into the catheter 100. For example, portions of device may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the catheter 100 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A medical device, comprising:
an elongated shaft including at least one reinforcement member, the reinforcement member selected from the group consisting of a braid, coil, wire, ribbon, or fiber;
an inner layer and an outer layer, the reinforcement member disposed therebetween;
the reinforcement member including a first portion and a second portion; and
the first portion having a first degree of polymeric crystallinity and the second portion having a second degree of polymeric crystallinity different than the first degree of polymeric crystallinity.

2. The medical device of claim 1, wherein the inner layer includes polytetrafluoroethylene.

3. The medical device of claim 1, wherein the inner layer includes fluorinated ethylene propylene.

4. The medical device of claim 1, wherein the outer layer includes polyether block amide.

5. The medical device of claim 1, wherein the outer layer includes a blend of polyether block amide and polyurethane.

6. The medical device of claim 1, wherein the reinforcement member is a polymeric braid.

7. The medical device of claim 1, wherein the reinforcement member is a polymeric coil.

8. The medical device of claim 1, wherein the reinforcement member includes an ultra-high molecular weight polyethylene braid.

9. The medical device of claim 1, wherein the second degree of polymeric crystallinity of the second portion is lower than the first degree of polymeric crystallinity of the first portion.

10. The medical device of claim 1, wherein the reinforcement member comprises at least two materials.

11. The medical device of claim 1, wherein the reinforcement member is at least partially embedded within the outer layer of the elongated shaft.

12. The medical device of claim 1, wherein the elongated shaft includes the reinforcement member and an axial reinforcement member.

13. The medical device of claim 1, wherein the reinforcement member is made of ultra-high molecular weight polyethylene.

14. A method for manufacturing a medical device, the method comprising:
forming an elongated shaft,
wherein forming the elongated shaft includes forming a reinforcement member made of ultra-high molecular weight polyethylene, the reinforcement member having a first portion and a second portion;
heating the elongated shaft;
wherein forming the elongated shaft comprises forming the reinforcement member as a polymeric braid; and
wherein heating the elongated shaft causes the first portion to have a first degree of polymeric crystallinity and the second portion to have a second degree of polymeric crystallinity different than the first degree of polymeric crystallinity.

15. The method of claim 14, wherein forming the elongated shaft comprises disposing the reinforcement member between an inner layer and an outer layer.

16. The method of claim 14, wherein heating the elongated shaft causes the second degree of polymeric crystallinity to be lower than the first degree of polymeric crystallinity.

17. The method of claim 14, wherein forming the elongated shaft comprises forming the reinforcement member from at least two materials.

18. A method for manufacturing a medical device, the method comprising:
forming an elongated shaft,
wherein forming the elongated shaft includes forming a reinforcement member made of ultra-high molecular weight polyethylene, the reinforcement member having a first portion and a second portion;
heating the elongated shaft;
wherein heating the elongated shaft causes the first portion to have a first degree of polymeric crystallinity and the second portion to have a second degree of polymeric crystallinity different than the first degree of polymeric crystallinity;
wherein forming the elongated shaft comprises disposing the reinforcement member between an inner layer and an outer layer; and
wherein the reinforcement member is selected from the group consisting of a braid, coil, wire, ribbon, or fiber.

* * * * *